United States Patent
Lippmann et al.

(10) Patent No.: US 9,193,646 B2
(45) Date of Patent: Nov. 24, 2015

(54) PROCESS FOR PROVIDING AROMATICS FROM COAL TAR

(71) Applicant: UOP LLC, Des Plaines, IL (US)

(72) Inventors: Matthew Lippmann, Chicago, IL (US); Paul T. Barger, Arlington Heights, IL (US); Maureen L. Bricker, Buffalo Grove, IL (US); Joseph A. Kocal, Glenview, IL (US); Kurt M. Vanden Bussche, Lake in the Hills, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/719,113

(22) Filed: May 21, 2015

(65) Prior Publication Data
US 2015/0251977 A1    Sep. 10, 2015

Related U.S. Application Data

(62) Division of application No. 14/462,738, filed on Aug. 19, 2014, now Pat. No. 9,073,811.

(60) Provisional application No. 61/905,969, filed on Nov. 19, 2013.

(51) Int. Cl.
| | | |
|---|---|---|
| *C10G 57/00* | (2006.01) | |
| *C10G 55/00* | (2006.01) | |
| *C07C 5/367* | (2006.01) | |
| *C10G 67/02* | (2006.01) | |
| *C10G 67/00* | (2006.01) | |
| *C10G 69/00* | (2006.01) | |

(52) U.S. Cl.
CPC ............... *C07C 5/367* (2013.01); *C10G 67/00* (2013.01); *C10G 67/02* (2013.01); *C10G 69/00* (2013.01)

(58) Field of Classification Search
USPC .......................... 208/49, 57, 88, 97, 107, 133
See application file for complete search history.

(56) References Cited

U.S. PATENT DOCUMENTS 3,556,987 A * 1/1971 Zimmerman, Jr. et al. ..... 208/93

* cited by examiner

*Primary Examiner* — Thuan D Dang

(57) ABSTRACT

A process for providing aromatics from a coal tar stream. A coal tar stream is provided, and the coal tar stream is fractionated into at least a naphtha range stream. The naphtha range stream is hydrotreated, and the hydrotreated naphtha range stream is separated to provide at least a naphthene rich stream. The naphthene rich stream is reformed or dehydrogenated to convert the naphthene. The dehydrogenated naphthene rich stream may be combined with a portion of a reformed crude oil hydrocarbon stream.

6 Claims, 2 Drawing Sheets

US 9,193,646 B2

PROCESS FOR PROVIDING AROMATICS FROM COAL TAR

CROSS-REFERENCE TO RELATED APPLICATIONS

This application is a Division of copending application Ser. No. 14/462,738 filed Aug. 19, 2014, which application claims priority from Provisional Application No. 61/905,969 filed Nov. 19, 2013, the contents of which are hereby incorporated by reference.

BACKGROUND OF THE INVENTION

Many different types of chemicals are produced from the processing of petroleum. However, petroleum is becoming more expensive because of increased demand in recent decades.

Therefore, attempts have been made to provide alternative sources for the starting materials for manufacturing chemicals. Attention is now being focused on producing liquid hydrocarbons from solid carbonaceous materials, such as coal, which is available in large quantities in countries such as the United States and China.

Pyrolysis of coal produces coke and coal tar. The coke-making or "coking" process consists of heating the material in closed vessels in the absence of oxygen to very high temperatures. Coke is a porous but hard residue that is mostly carbon and inorganic ash, which may be used in making steel.

Coal tar is the volatile material that is driven off during heating, and it comprises a mixture of a number of hydrocarbon compounds. It can be separated to yield a variety of organic compounds, such as benzene, toluene, xylene, naphthalene, anthracene, and phenanthrene. These organic compounds can be used to make numerous products, for example, dyes, drugs, explosives, flavorings, perfumes, preservatives, synthetic resins, and paints and stains. The residual pitch left from the separation is used for paving, roofing, waterproofing, and insulation.

Coal tar is rich in aromatics, but includes a large portion of contaminants, such as sulfur, nitrogen, metals, mercury, oxygenates, etc. Removing such contaminants saturates the aromatics. There is a need for an improved process for providing aromatics from coal tar.

SUMMARY OF THE INVENTION

One aspect of the invention involves a process for providing aromatics from a coal tar stream. A coal tar stream is provided, and the coal tar stream is fractionated into at least a naphtha range stream. The naphtha range stream is hydrotreated, and the hydrotreated naphtha range stream is separated to provide at least a naphthene rich stream. The naphthene rich stream is reformed to convert the naphthenes to aromatics and provide an aromatic stream.

Another aspect of the invention involves a process for providing aromatics. A coal tar stream is provided, and the coal tar stream is fractionated into at least a naphtha range stream. The naphtha range stream is hydrotreated, and the hydrotreated naphtha range stream is separated to provide at least a naphthene rich stream. The naphthene rich stream is dehydrogenated to convert naphthenes in the naphthene rich stream to aromatics.

DETAILED DESCRIPTION OF THE INVENTION

Figure 1:
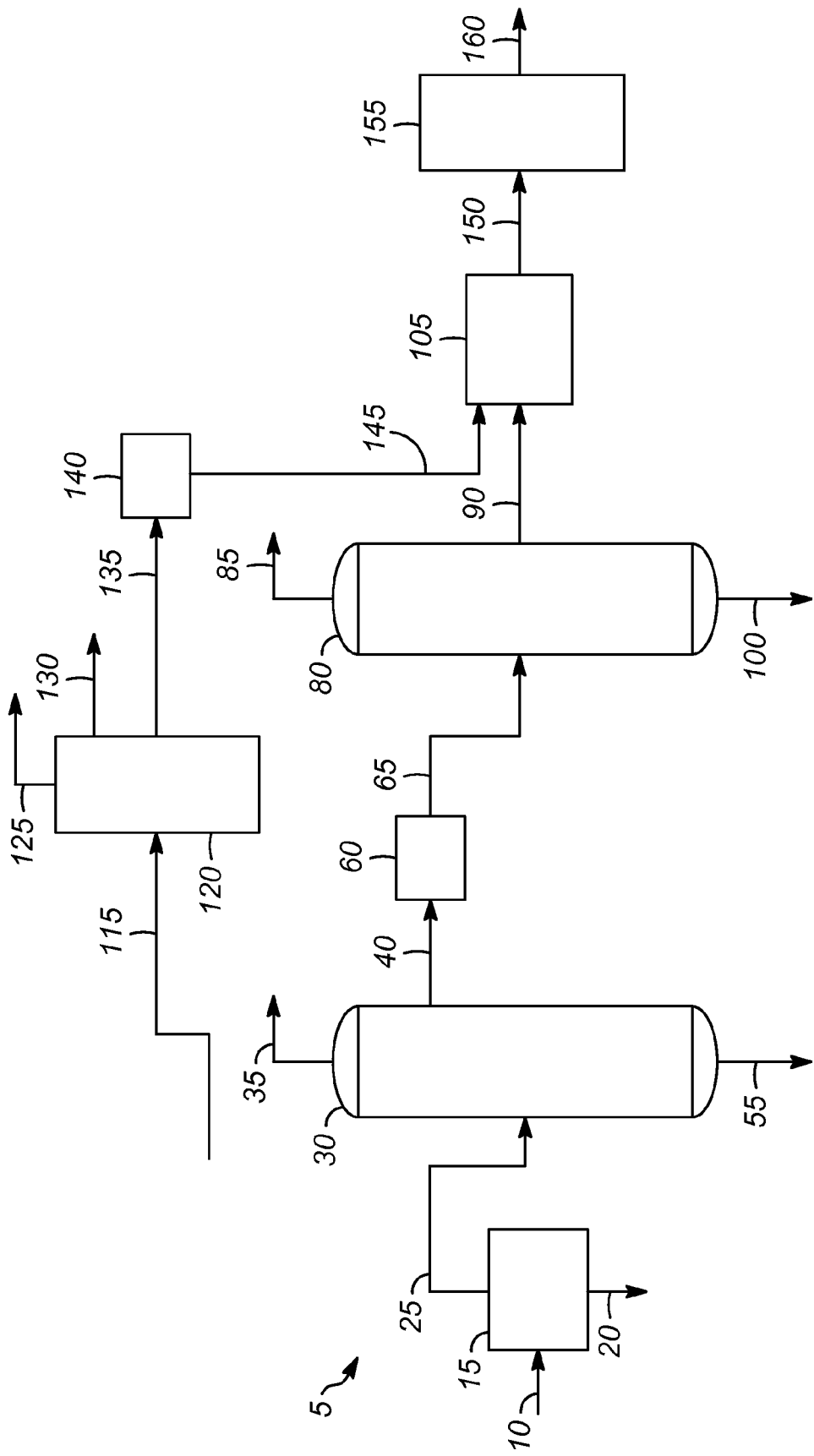
FIG. 1 is an illustration of a first embodiment of the process of the present invention.

FIG. 1 shows a first embodiment of a coal conversion process 5. A coal feed 10 is sent to a pyrolysis zone 15. In some processes, all or a portion of the coal feed 10 is also sent to a gasification zone (not shown), where the coal feed 10 is mixed with oxygen and steam and reacted under heat and pressure to form syngas, which is a mixture of carbon monoxide and hydrogen. The syngas can be further processed using the Fischer-Tropsch reaction to produce gasoline or using the water-gas shift reaction to produce more hydrogen. The coal feed 10 can be sent to the pyrolysis zone 15, the gasification zone, or the coal feed 10 can be split into two parts and sent to both.

In the pyrolysis zone 15, the coal feed 10 is heated at high temperature, e.g., up to about 2,000° C. (3,600° F.), in the absence of oxygen to drive off the volatile components. Pyrolysis produces a coke stream 20 and a coal tar stream 25. The coke stream 20 can be used in other processes, such as the manufacture of steel.

The coal tar stream 25, or a coal tar stream obtained from other sources, is delivered to a fractionation zone 30. Coal tar comprises a complex mixture of heterocyclic aromatic compounds and their derivatives with a wide range of boiling points. The number of fractions and the components in the various fractions can be varied as is well known in the art. A typical separation process involves separating the coal tar into four to six streams. For example, there can be a fraction comprising NH3, CO, and light hydrocarbons, a light oil fraction with boiling points between 0° C. and 180° C., a middle oil fraction with boiling points between 180° C. to 230° C., a heavy oil fraction with boiling points between 230 to 270° C., an anthracene oil fraction with boiling points between 270° C. to 350° C., and pitch.

The light oil fraction contains compounds such as benzenes, toluenes, xylenes, naphtha, coumarone-indene, dicyclopentadiene, pyridine, and picolines. The middle oil fraction contains compounds such as phenols, cresols and cresylic acids, xylenols, naphthalene, high boiling tar acids, and high boiling tar bases. The heavy oil fraction contains creosotes. The anthracene oil fraction contains anthracene. Pitch is the residue of the coal tar distillation containing primarily aromatic hydrocarbons and heterocyclic compounds.

In the process 5, the coal tar stream 25 is fractionated to provide at least a full range naphtha stream 40, which is a highly aromatic stream. The example full range naphtha stream 40 comprises hydrocarbons in the $C_5$-$C_{13}$ range. Fractionation can also provide, for instance, a fraction comprising $NH_3$, CO, and light hydrocarbons 35, and a pitch stream 55.

The full range naphtha stream 40 is sent to a hydrotreating zone 60 for removing contaminants. Hydrotreating is a process in which hydrogen gas is contacted with a hydrocarbon stream in the presence of suitable catalysts which are primarily active for the removal of heteroatoms, such as sulfur, nitrogen, and metals from the full range naphtha stream 40.

The hydrotreating in the hydrotreating zone 60 preferably takes place under conditions that are more severe than for a typical naphtha hydrotreating process. Example conditions include a pressure between about 6.89 MPa (1,000 psig) to about 13.8 MPa (2,000 psig) and a temperature greater than about 316° C. (600° F.). An example catalyst for the hydrotreating zone 60 is 10-20% molybdenum, 5-10% cobalt and nickel. The hydrotreating removes contaminants such as sulfur, nitrogen, mercury, metals, oxygenates, etc. The hydrotreating also saturates aromatics in the full range naphtha stream 40, making the hydrotreated stream rich in naphthenes.

The hydrotreated stream 65 is fed to a separation zone 80. An example separation zone 80 is a naphtha splitter, for example a distillation column. The separation zone 80 separates the hydrotreated stream 65 into at least a naphthene rich stream 90, e.g., in the $C_6$-$C_{10}$ range. The separation zone may further separate the hydrotreated stream 65 into a light hydrocarbon ($C_5$-) stream 85 and a heavy aromatics ($C_{11}$+) stream 100. The light hydrocarbon stream 85 can be, for instance, combined with a liquefied petroleum gas (LPG) stream or gasoline stream.

The naphthene rich stream 90 is sent to a reforming zone 105 for converting the naphthenes to aromatics to provide an aromatic stream 150. Reforming is a catalytic process for producing aromatics from paraffins and naphthenes by rearranging or restructuring hydrocarbon molecules and breaking larger hydrocarbon molecules into smaller ones. Hydrogen is produced as a byproduct. An example reforming process is the CCR PLATFORMING™ catalytic reforming process (UOP, Des Plaines, Ill.), which includes dehydrogenation of naphthenes, isomerization of paraffins and naphthenes, dehydrogenation of paraffins, paraffin hydrocracking, and dealkylation of aromatics. An example reforming process includes a catalyst that is continuously regenerated in a regeneration section.

An example reforming zone 105 is a high severity catalytic reforming zone. Example conditions include a pressure between about 344 kPa (50 psig) and about 1,379 kPa (200 psig), a temperature of between about 510° C. (950° F.) and about 566° C. (1,050° F.). Example catalysts include platinum and tin catalysts. Liquid hourly space velocity (LHSV) can vary, and can be selected to provide a desired reformate.

In the process 5, the naphthene rich stream 90 is combined with a stream from a crude oil feed before reforming. Particularly, a crude oil feed 115 is sent to a crude oil fractionation zone 120, for example a fractionation column, where the crude oil feed is fractionated into a liquefied petroleum gas (LPG) stream 125, a light naphtha stream 130, and a crude oil hydrocarbon stream 135, for example a $C_6$-$C_{10}$ stream. The crude oil hydrocarbon stream 135 is sent to a hydrotreating zone 140.

The hydrotreating zone 140 preferably operates at less severe conditions than the hydrotreating zone 60 for the naphtha range stream 40. Typical hydrotreating reaction conditions include a temperature of about 290° C. (550° F.) to about 455° C. (850° F.), a pressure of about 3.4 MPa (500 psig) to about 26.7 MPa (4,000 psig), a liquid hourly space velocity of about 0.5 $hr^{-1}$ to about 4 $hr^{-1}$, and a hydrogen rate of about 168 to about 1,011 $Nm^3/m^3$ oil (1,000-6,000 scf/bbl). Typical hydrotreating catalysts include at least one Group VIII metal, preferably iron, cobalt and nickel, and at least one Group VI metal, preferably molybdenum and tungsten, on a high surface area support material, preferably alumina. Other typical hydrotreating catalysts include zeolitic catalysts, as well as noble metal catalysts where the noble metal is selected from palladium and platinum.

Example conditions for the hydrotreating zone 140 include a pressure between about 3.48 MPa (about 500 psig) and about 4.83 MPa (about 700 psig), and a temperature less than about 302° C. (about 575 F). Example catalysts include 9-12% molybdenum, 3% cobalt catalysts. A hydrotreated stream 145 from the hydrotreating zone 140 is reformed in the reforming zone 105 with the naphthene rich stream 90. For example, both the hydrotreated stream 145 from crude oil and the naphthene rich stream 90 can be co-fed into the reforming zone 105, or the hydrotreated stream and the naphthene rich stream can be combined and then fed into the reforming zone 105.

The aromatic stream 150 output from the reforming zone 105 is a reformate stream that includes aromatics converted from the naphthenes in the naphthene rich feed 90, and aromatics converted from naphthenes and paraffins from the crude oil based hydrotreated stream 145. The aromatic stream 150 can be fed to a recovery zone 155 for recovering aromatics, such as benzene, toluene, and xylene, from the aromatic stream and providing at least one recovered aromatics stream 160. An example recovery zone 155 can include, for example, a reformate splitter, one or more separation zones, for separating xylenes and para-xylenes, solvent extraction and distillation zones for extracting benzene and toluene, transalkylation zones for transalkylating toluene to produce benzene and xylenes, and isomerization zones for isomerization of xylenes and conversion of ethyl benzene to xylenes. Hydrotreating may be provided at stages to remove contaminants. One or more of these processes may be omitted in particular embodiments depending on the products desired. Example conditions for the recovery zone 155 will be appreciated by those of ordinary skill in the art.

Figure 2:
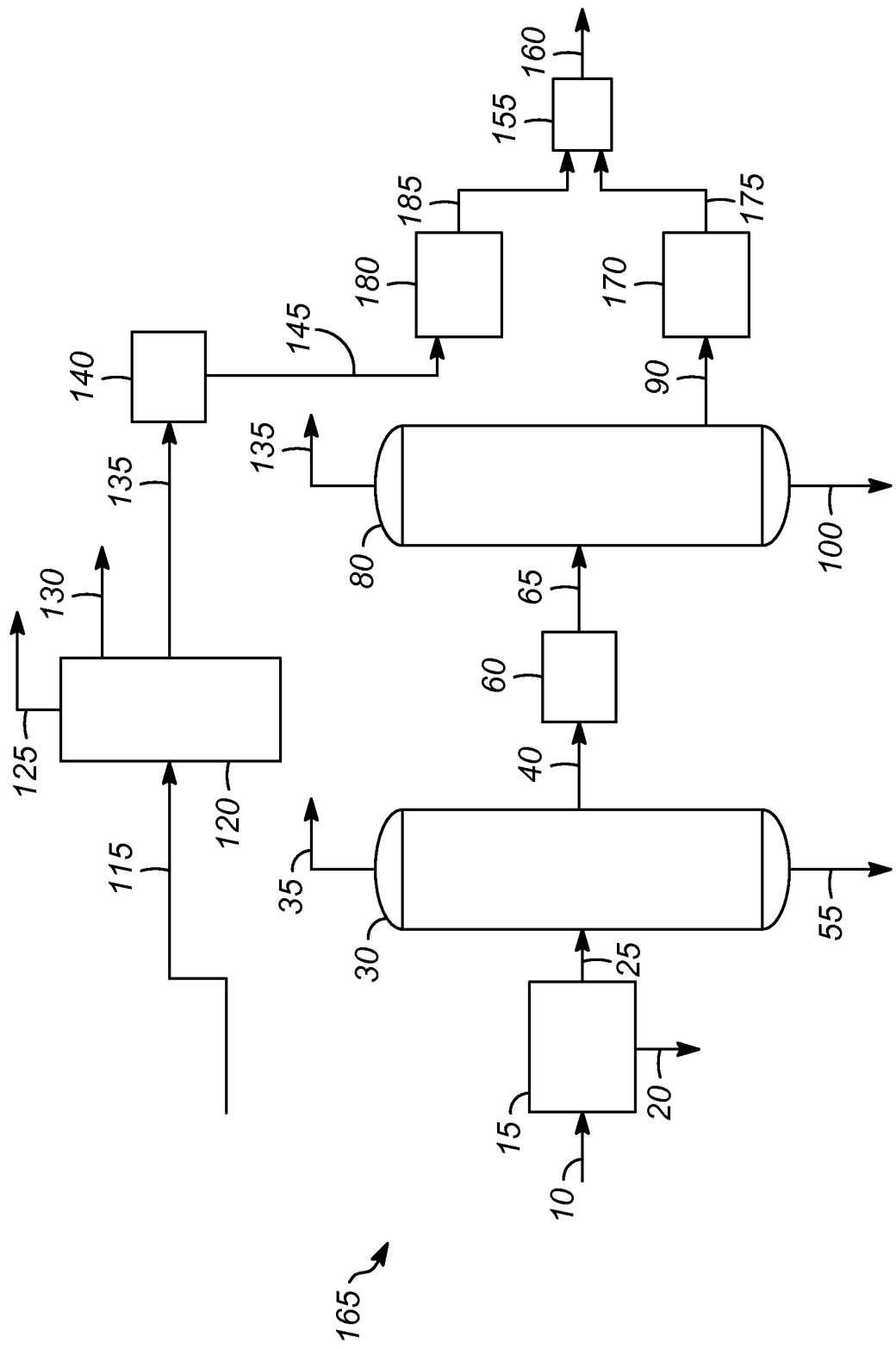
FIG. 2 is an illustration of a second embodiment of the process of the present invention.

FIG. 2 shows a second embodiment of a coal conversion process 165, where like reference characters refer to like features. In the process 165, the naphthene rich stream 90 from the separation zone 80 (i.e., after severe hydrotreating in the hydrotreating zone 60) is fed to a dehydrogenation zone 170 for converting naphthenes in the naphthene rich stream 90 to aromatics. The process 165 takes advantage of easier reforming requirements for a naphthenic feed as opposed to paraffins in the crude oil hydrocarbon stream 135 from the crude oil feed 115. Because the coal tar stream 25 is lower in paraffins, it can be more efficient to convert the naphthenes in the naphthene rich stream 90 back to aromatics, at a lower severity than a reforming process, without dealkylating aromatics already in the stream.

Example configurations and conditions for the dehydrogenation zone 170 are disclosed in U.S. Pat. Nos. 4,762,960; 3,761,531; 4,880,764; and 4,048,245. The dehydrogenation zone 170 can include, for example, a configuration similar to the reforming zone 180 but be operated under dehydrogenation reaction conditions. Dehydrogenation reaction conditions can include a temperature of from about 400° to about 900° C., a pressure of from about 0.01 to 10 atmospheres and a liquid hourly space velocity (LHSV) of from about 0.1 to 100 $hr^{-1}$. Generally, for normal paraffins, the lower the molecular weight, the higher the temperature required for comparable conversion. The pressure in the dehydrogenation zone 170 is preferably maintained as low as practicable, consistent with equipment limitations, to maximize the chemical equilibrium advantages. The preferred dehydrogenation conditions of the process of this invention include a temperature of from about 400° to 700° C., a pressure from about 0.1 to 5 atmospheres, and a liquid hourly space velocity of from about 0.1 to 100 $hr^{-1}$.

The dehydrogenatable hydrocarbons may be admixed with a diluent gas before, while, or after being passed to the dehydrogenation zone 170. The diluent material may be hydrogen, steam, methane, carbon dioxide, nitrogen, argon and the like or a mixture thereof. Hydrogen is the preferred diluent. Ordinarily, when a diluent gas is utilized, it is used in amounts sufficient to ensure a diluent gas to hydrocarbon mole ratio of about 0.1 to about 20, with best results being obtained when the mole ratio range is about 0.5 to 10. The diluent hydrogen stream passed to the dehydrogenation zone 170 will typically be recycled hydrogen separated from an effluent from the dehydrogenation zone 170 in a hydrogen separation zone (not shown).

Preferred dehydrogenation reaction conditions include a pressure of between about 0.689 MPa (100 psig) and about 2.07 MPa (about 300 psig), and a temperature of between about 482° C. (900° F.) and about 538° C. (1000° F.). Example catalysts include platinum catalysts, or platinum and tin catalysts. The dehydrogenation zone 170 provides a dehydrogenated naphthene rich stream 175 in which naphthenes in the naphthene rich stream are converted to aromatics.

The hydrotreated stream 145 from crude oil is fed to a reforming zone 180, which can be similar to the reforming zone 105 in the process 5 of FIG. 1. Example conditions include a pressure between about 344 kPa (50 psig) and about 1378 kPa (200 psig), a temperature of between about 510° C. (950° F.) and about 566° C. (1050° F.). As opposed to the process 5 of FIG. 1, in the process 165 the naphthene rich stream 90 from the coal tar feed 25 is not fed to the reforming zone 180. Instead, naphthenes from the naphthene rich stream 90 are converted in the dehydrogenation zone 170, and the hydrotreated stream 145, which is more paraffinic than the naphthene rich stream, is reformed in the reforming zone 180.

A reformate stream 185 from the reforming zone 180 and the dehydrogenated naphthene rich stream 175 are combined to provide a combined stream and sent to the recovery zone 155 for recovering aromatics and provide at least one recovered aromatics stream 160. For example, the reformate stream 185 and the naphthene rich stream 175 can be co-fed into the recovery zone 155, or the reformate stream and the naphthene rich stream can be combined and then fed into the recovery zone. Configuration and operation of the recovery zone 155 can be similar to that for process 5 of FIG. 1.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

The invention claimed is:

1. A process comprising:
providing a coal tar stream;
fractionating the coal tar stream into at least a naphtha range stream containing aromatics;
hydrotreating the naphtha range stream in the presence of a catalyst containing molybdenum, cobalt and nickel to remove contaminants including sulfur, nitrogen, mercury, metals, or oxygenates and to saturate aromatics to produce a hydrotreated stream rich in naphthenes;
separating the hydrotreated naphtha stream to provide at least a naphthene rich stream in the $C_6$-$C_{10}$ range; and a light hydrocarbon stream comprising C5-hydrocarbons;
dehydrogenating the naphthene rich stream to convert naphthene rich stream to aromatics to produce a dehydrogenated naphthene rich stream;
provide a crude oil hydrocarbon stream containing naphthenes and paraffins from a crude oil feed;
hydrotreating the crude oil hydrocarbon stream in the presence of catalyst containing at least one group VIII metal and at least one group VI metal under a condition less severe than the condition of hydrotreating of the naphtha range stream to produce a hydrotreated crude oil hydrocarbon stream;
combining the dehydrogenated naphthene rich stream with the hydrotreated crude oil hydrocarbon stream to form a combined stream; and
reforming the combined stream to convert the naphthenes to aromatics and provide an aromatic stream.

2. The process of claim 1 wherein the hydrotreating the naphtha range stream takes place at a pressure between about 6.89 MPa (1,000 psig) to about 13.8 MPa (2,000 psig) and a temperature greater than about 316° C. (600° F.).

3. The process of claim 1 wherein providing a coal tar stream comprises pyrolyzing a coal feed to provide a coke stream and the coal tar stream.

4. The process of claim 1 wherein the dehydrogenation takes place at a pressure between about 0.689 MPa (100 psig) to about 2.07 MPa (300 psig) and a temperature of between about 482° C. (900° F.) and about 538° C. (1000° F.).

5. The process of claim 1 wherein the naphthene rich stream comprises $C_6$ to $C_{10}$ aromatic hydrocarbons.

6. The process of claim 1 further comprising fractionating a crude oil stream to provide the crude oil hydrocarbon stream, wherein the crude oil hydrocarbon stream comprises $C_6$ to $C_{10}$ hydrocarbons.

* * * * *